(12) United States Patent
Fuhrmann et al.

(10) Patent No.: US 8,053,426 B2
(45) Date of Patent: Nov. 8, 2011

(54) PROGESTERONE RECEPTOR ANTAGONISTS

(75) Inventors: Ulrike Fuhrmann, Berlin (DE); Anja Schmidt, Berlin (DE); Arwed Cleve, Berlin (DE); Orlin Petrov, Berlin (DE); Gunnar Garke, Berlin (DE); Stefan Pruehs, Neuss (DE); Margarete Brudny-Kloeppel, Berlin (DE); Antje Rottmann, Berlin (DE); Rainer Hasselmann, Berlin (DE); Marcus Schultze-Mosgau, Berlin (DE); Carsten Moeller, Berlin (DE)

(73) Assignee: Bayer Schering Pharma AG, Berlin (DE)

( * ) Notice: Subject to any disclaimer, the term of this patent is extended or adjusted under 35 U.S.C. 154(b) by 482 days.

(21) Appl. No.: 11/984,331

(22) Filed: Nov. 15, 2007

(65) Prior Publication Data
US 2008/0200440 A1 Aug. 21, 2008

Related U.S. Application Data

(60) Provisional application No. 60/858,955, filed on Nov. 15, 2006.

(30) Foreign Application Priority Data

Nov. 15, 2006 (DE) .................. 10 2006 054 535

(51) Int. Cl.
*A61K 31/565* (2006.01)
*C07J 1/00* (2006.01)
(52) U.S. Cl. ....................... 514/179; 552/648
(58) Field of Classification Search .................. 514/179; 552/648
See application file for complete search history.

(56) References Cited

U.S. PATENT DOCUMENTS

| | | | |
|---|---|---|---|
| 4,609,651 | A | 9/1986 | Rohde et al. |
| 4,900,725 | A | 2/1990 | Nioue et al. |
| 5,712,264 | A | 1/1998 | Hamersma et al. |
| 6,225,298 | B1 | 5/2001 | Spicer et al. |
| 6,316,432 | B1 | 11/2001 | Schwede et al. |
| 6,825,182 | B2 | 11/2004 | Ring et al. |
| 2001/0016578 | A1 | 8/2001 | Spicer et al. |
| 2002/0143000 | A1 | 10/2002 | Hegele-Hartung et al. |

FOREIGN PATENT DOCUMENTS

| | | |
|---|---|---|
| CA | 2280041 | 8/1998 |
| WO | WO 98/05679 | 2/1992 |
| WO | WO 98/05679 | 2/1998 |
| WO | WO-98 34947 | 8/1998 |
| WO | WO 02/32429 * | 4/2002 |
| WO | WO-03 093292 | 11/2003 |
| WO | WO 2008/058767 A1 | 5/2008 |

OTHER PUBLICATIONS

Fuhrmann U et al, "Synthesis and Biological Activity of a Novel, Highly Potent Progesterone Receptor Antagonist", Journal of Medicinal Chemistry, American Chemical Society, Washington, US, vol. 43, No. 26, 2000, pp. 5010-5016, XP001064233.

Bagaria, M., et al., "Low-dose mifepristone in treatment of uterine leiomyoma: A randomized double-blind placebo-controlled clinical trial," Australian and New Zealand Journal of Obstetrics and Gynaecology 2009; 49: 77-83.

Chwalisz, K., M.D., Ph.D., et al., "A randomized, controlled trial of asoprisnil, a novel selective progesterone receptor modulator, in women with uterine leiomyomata," Fertility and Sterility, vol. 87, No. 6, Jun. 2007, 1399-1412.

Furhmann, U., et al., "Synthesis and Biological Activity of a Novel, Highly Potent Progesterone Receptor Antagonist," J. Med. Chem. 2000, 43, 5010-5016.

Kettel, L.M., M.D., et al., "Preliminary report on the treatment of endometriosis with low-dose mifepristone (RU 486)," Am. J. Obstet. Gynecol. 1998; 178: 1151-1156.

Kettel, L.M., M.D et al., "Treatment of endometriosis with the antiprogesterone mifepristone (RU 486)†‡," Fertility and Sterility, vol. 65, No. 1, Jan. 1996, 23-28.

Kettel, L.M., M.D., et al., "Endocrine responses to long-term administration of the antiprogesterone RU 486 in patients with pelvic endometriosis †," Fertility and Sterility, vol. 56, No. 3, Sep. 1991, 402-407.

Moller, C., et al., "Investigational developments for the treatment of progesterone-dependent diseases," Expert Opin. Investig. Drugs (2008) 17(4): 469-479.

Murphy, A.A., et al., "Regression of uterine leiomyomata in response to the antiprogesterone RU 486," The J. Clin. Endocrinol. Metab, 1993 76: 513-517.

Steinauer, J., M.D., et al., "Systematic Review of Mifepristone for the Treatment of Uterine Leiomyomata," American College of Obeste. and Gynecol., vol. 103, No. 6, Jun. 2004, 1331-1336.

* cited by examiner

*Primary Examiner* — Barbara P Badio
(74) *Attorney, Agent, or Firm* — Millen, White, Zelano & Branigan, P.C.

(57) ABSTRACT

The present invention relates to progesterone receptor antagonists of general formula I:

formula I in which R1 can be a hydrogen atom and R2 a hydroxyl group or R1 and R2 together can be an oxo group.

28 Claims, 2 Drawing Sheets

PROGESTERONE RECEPTOR ANTAGONISTS

This application claims the benefit of the filing date of U.S. Provisional Application Ser. No. 60/858,955 filed Nov. 15, 2006.

The present invention relates to progesterone receptor antagonists of general formula I:

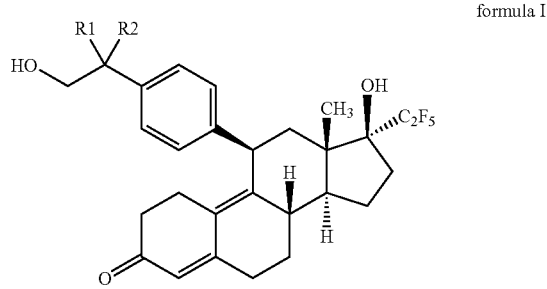

formula I in which R1 can be a hydrogen atom and R2 a hydroxyl group or R1 and R2 together can be an oxo group, to drugs (pharmaceutical compositions) containing them and to their use in the manufacture of medicaments.

The invention relates in particular to the progesterone receptor antagonists

11β-[4-(1,2-dihydroxyethyl)phenyl]-20,20,21,21,21-pentafluoro-17-hydroxy-19-nor-17α-pregna-4,9-dien-3-one and its individual epimers 11β-[4-[(1R)-1,2-dihydroxyethyl]phenyl]-20,20,21,21,21-pentafluoro-17-hydroxy-19-nor-17α-pregna-4,9-dien-3-one and 11β-[4-[(1S)-1,2-dihydroxyethyl]phenyl]-20,20,21,21,21-pentafluoro-17-hydroxy-19-nor-17α-pregna-4,9-dien-3-one and 20,20,21,21,21-pentafluoro-17-hydroxy-11β-[4-(hydroxyacetyl)phenyl]-19-nor-17α-pregna-4,9-dien-3-one and to drugs containing them and to their use in the manufacture of medicaments.

A preferred compound of this invention is 20,20,21,21,21-Pentafluoro-17-hydroxy-11β-[4-(hydroxyacetyl)phenyl]-19-nor-17α-pregna-4,9-dien-3-one.

Compounds with antigestagenic activity (competitive progesterone receptor antagonists) first became known in 1982 (RU 486; EP57115) and have since been very well described. Steroids with antigestagenic activity which are different from the substances according to the invention and have a fluorinated 17α side chain were published in WO98/34947 and Fuhrmann et al., J. Med. Chem. 43, 5010-5016 (2000). The class of compounds disclosed in WO98/34947 permitted a large variety of substituents at position-11 of the steroid nucleus but did not extent to disubstituted alkylphenyl groups. EP57115 allowed a range of substituents at position 11 of the steroid nucleus but required that such substituents contained a nitrogen, phosphorus or silicon atom. There is therefore no suggestion that steroids containing a fluorine containing substituent at position 17 and a disubstituted alkylphenyl substituent at position 11 of the steroid nucleus could have desirable properties.

Substances claimed here are at least partially metabolites of a substance claimed in WO98/34947.

The object of the present invention is to provide novel competitive progesterone receptor antagonists and drugs containing them and hence to create alternative ways of treating gynecological diseases.

The object has been achieved by the synthesis of 11β-[4-(1,2-dihydroxyethyl)phenyl]-20,20,21,21,21-pentafluoro-17-hydroxy-19-nor-17α-pregna-4,9-dien-3-one and 20,20,21,21,21-pentafluoro-17-hydroxy-11β-[4-(hydroxyacetyl)phenyl]-19-nor-17α-pregna-4,9-dien-3-one. The epimers of 11β-[4-(1,2-dihydroxyethyl)phenyl]-20,20,21,21,21-pentafluoro-17-hydroxy-19-nor-17α-pregna-4,9-dien-3-one can be specifically prepared either by means of chromatographic separation on a Chiracel OD-H column with hexane/ethanol 90:10 (v/v) as mobile phase, or by starting from chiral structural entities such as (R)- or (S)-1-(4-bromophenyl)-1,2-ethanediol.

The compounds of this invention are therefore favourable those that have been prepared by chemical processes.

Aptly the invention provides a dihydroxy compound of this invention substantially free of its isomer, that is when in at least 90%, more aptly at least 95% preferably at least 98% and most preferably 100% free from the corresponding isomer.

Since the compounds of the invention are to be used in pharmaceutical compositions it is favoured to provide then is isolated form, for example as a solid, aptly as a substantially pure solid, for example substantially free of other steroidal compounds or other biologically active agents.

Substances of general formula I are valuable pharmaceutical active ingredients. They can be used inter alia for the manufacture of pharmaceutical preparations for the treatment of myomas or endometriosis, for female contraception, for postcoital fertility control, for bringing on menstruation, for inducing labor, for hormone replacement therapy, for the treatment of symptoms associated with dysmenorrhea, for the treatment of hormonal irregularities and for the treatment of hormone-dependent tumors, e.g. a progesterone receptor-positive carcinoma of the breast. Their efficacy as progesterone receptor antagonists has been identified in the abortion test on the rat and by determination of the McPhail index on the rabbit.

The substances of general formula I exhibit a higher metabolic stability in human liver microsomes (HLM) than the progesterone receptor antagonist 11β-(4-acetylphenyl)-20,20,21,21,21-pentafluoro-17-hydroxy-19-nor-17α-pregna-4,9-dien-3-one disclosed in WO98/34947. This is indicative of enhanced oral bioavailability of the compounds of this invention so that they can be used in pharmaceutical compositions adapted for oral administration.

The drugs (pharmaceutical compositions) according to the invention can be adapted for systemic or local administration. Generally it is preferred to adapt the drugs for systemic administration, for example by injection or by oral administration. If injectable form are contemplated these may be prepared by conventional methods known in the art for formulating steroids. If orally administrable forms are contemplated these may also be prepared by conventional methods known in the pharmaceutical arts for formulating steroids.

Preferred forms of the drugs will comprise a compound of the formula 1 and a pharmaceutically acceptable carrier therefore.

The pharmaceutical composition of the invention may be provided in a form suitable for systemic or local administration of which a systemically administrable form is generally is most apt. The systemically administrable form may be adapted for administration by injection, for example as a sterile form, for example an emulsion. The systemically administrable form may be adapted for oral administration and such forms are generally most suitable. Such forms generally will be a unit dosage form containing a predetermined amount of the compound of the invention. Suitable forms include tablets, capsules, powders, granulated and the like of which tablets are generally preferred. Such dosage forms can be manufactured in conventional manner and the pharmaceutically acceptable carrier can be any suitable carrier especially a carrier known to be if use in formulation steroidal medicaments.

The unit dosage form may contain 0.01-100 mg of the claimed substances.

Figure 1:
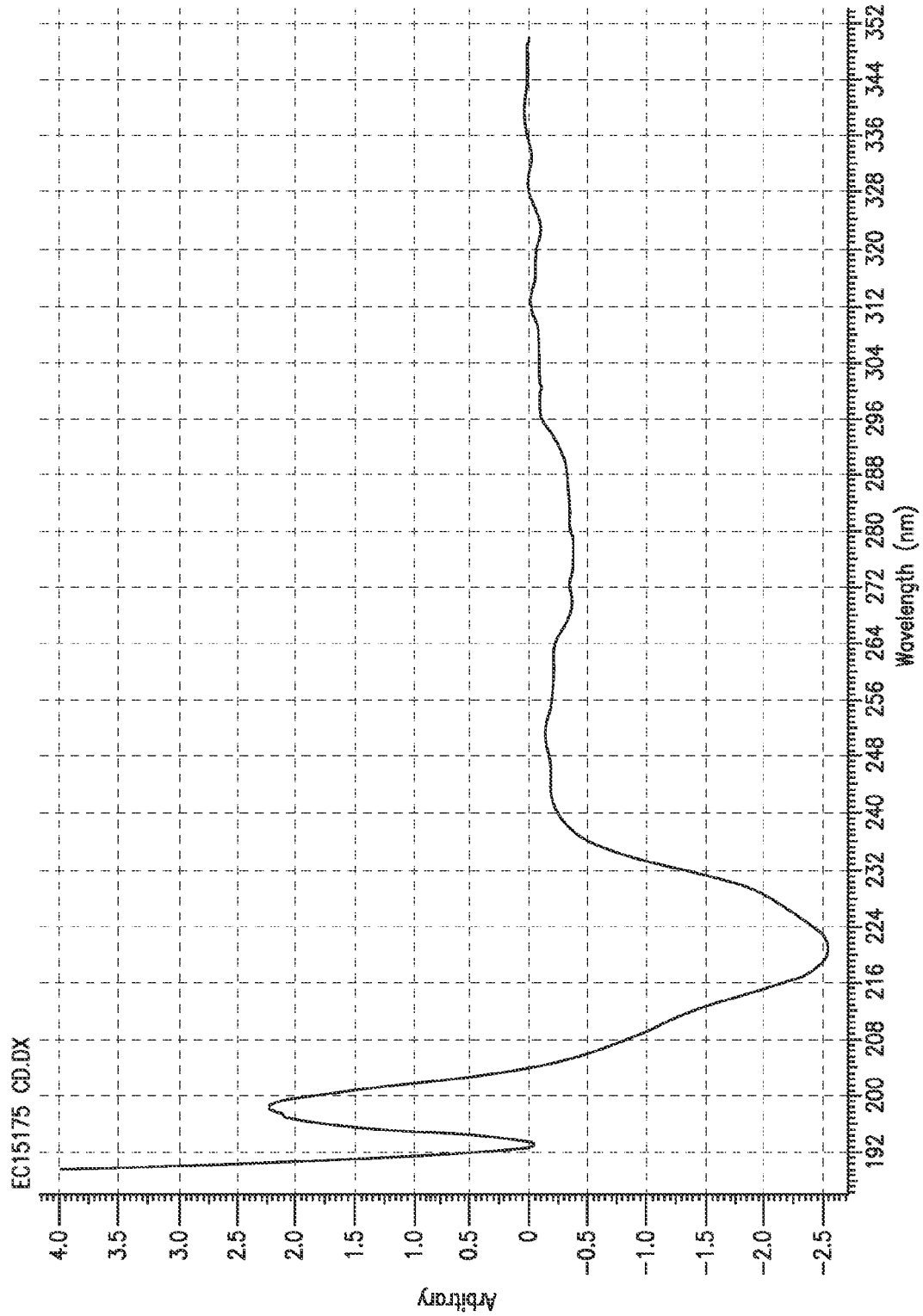
FIGS. 1 and 2 show CD spectra.

The Examples which follow serve to illustrate the invention without in any way implying a limitation.

EXAMPLE 1

Synthesis of 11β-[4-(1,2-dihydroxyethyl)phenyl]-20,20,21,21,21-pentafluoro-17-hydroxy-19-nor-17α-pregna-4,9-dien-3-one a) 11β-(4-Ethenylphenyl)-5-hydroxy-5α-estr-9-ene-3,17-dione 3-(2,2-dimethyl-propane-1,3-diyl) ketal 3.3 g of magnesium turnings are placed in 14 ml of absolute tetrahydrofuran under inert gas and one drop of 1,2-dibromoethane is added. After the reaction has started, a solution of 25 g of 4-bromostyrene in 137 ml of absolute tetrahydrofuran is slowly added dropwise so that the internal temperature remains in the range from 40 to 45° C. The reaction mixture is subsequently stirred for one hour until the magnesium has completely reacted. 2.26 g of copper(I) chloride are then added to the mixture. A solution of 8.5 g of 5,10-epoxy-5α,10α-estr-9(11)-ene-3,17-dione 3-(2,2-dimethylpropane-1,3-diyl) ketal (for preparation cf. *Tetrahedron Lett.* 26, 2069-2072 (1985)) in 137 ml of absolute tetrahydrofuran is slowly added dropwise. The reaction mixture is stirred for one hour at room temperature and then poured into saturated aqueous ammonium chloride solution. The aqueous phase is extracted with ethyl acetate and the organic phases are combined, washed with saturated aqueous sodium chloride solution and dried over sodium sulfate. The product is filtered and concentrated under vacuum. Column chromatography on silica gel with a hexane/ethyl acetate mixture gives 6.76 g of the title compound as a colorless foam.

$^1$H-NMR (300 MHz, CDCl$_3$): δ=7.30 d (J=9 Hz, 2H, aryl); 7.18 d (J=9 Hz, 2H, aryl); 6.66 dd (J=17 Hz+11 Hz, 1H, vinyl); 5.70 dbr (J=17 Hz, 1H, vinyl); 5.20 dbr (J=11 Hz, 1H, vinyl); 4.44 s (1H, 5-OH); 4.29 dbr (J=6.5 Hz, 1H, H-11); 3.53 m (2H, 3-ketal); 3.51 m (J=11.4 Hz, 1H, 3-ketal); 3.42 m (J=11.4 Hz, 1H, 3-ketal); 1.05 s (3H, 3-ketal); 0.85 s (3H, 3-ketal); 0.49 s (3H, H-18).

b) 11β-(4-Ethenylphenyl)-20,20,21,21,21-pentafluoro-5,17-dihydroxy-19-nor-5α,17α-pregn-9-en-3-one 2,2-dimethylpropane-1,3-diyl ketal A solution of 6.76 g of the compound prepared under a) in 140 ml of absolute toluene is added at −78° C. to 27.9 g of condensed pentafluoro-iodoethane in 140 ml of absolute toluene. 66.3 ml of a 1.5 molar solution of methyllithium/lithium bromide complex in diethyl ether are added at this temperature. The reaction mixture is subsequently stirred for one hour at 0° C. It is then poured into saturated aqueous ammonium chloride solution. The product is extracted with ethyl acetate, washed with saturated aqueous sodium chloride solution, dried over sodium sulfate and concentrated under vacuum. Chromatography of the resulting crude product on silica gel with a hexane/ethyl acetate mixture gives 3.73 mg of the title compound as a white foam.

$^1$H-NMR (300 MHz, CDCl$_3$): δ=7.30 d (J=9 Hz, 2H, aryl); 7.17 d (J=9 Hz, 2H, aryl); 6.67 dd (J=17 Hz+11 Hz, 1H, vinyl); 5.71 dbr (J=17 Hz, 1H, vinyl); 5.20 dbr (J=11 Hz, 1H, vinyl); 4.45 s (1H, 5-OH); 4.31 dbr (J=6.5 Hz, 1H, H-11); 3.53 m (2H, 3-ketal); 3.51 m (J=11.4 Hz, 1H, 3-ketal); 3.42 m (J=11.4 Hz, 1H, 3-ketal); 1.05 s (3H, 3-ketal); 0.85 s (3H, 3-ketal); 0.54 s (3H, H-18).

c) 11β-[4-(1,2-Dihydroxyethyl)phenyl]-20,20,21,21,21-pentafluoro-5,17-dihydroxy-19-nor-5α,17α-pregn-9-en-3-one 2,2-dimethylpropane-1,3-diyl ketal 1.68 ml of an aqueous buffer solution at pH 7.00 of potassium dihydrogen phosphate and dipotassium hydrogen phosphate and 206 mg of trimethylamine N-oxide are added to a solution of 1 g of the compound prepared according to Example 1b) in 8.4 ml of tetrahydrofuran. 4.3 ml of a solution of 250 mg of osmium tetroxide in 50 ml of butanol are added dropwise at 0° C. The reaction mixture is stirred for three hours at room temperature and then poured into saturated aqueous sodium thiosulfate solution. The product is extracted with ethyl acetate, washed with saturated aqueous sodium chloride solution, dried over sodium sulfate and concentrated under vacuum. Chromatography of the resulting crude product on silica gel with a hexane/ethyl acetate mixture gives 860 mg of the title compound as a white foam. A mixture of epimers at the benzylcarbinol is obtained.

$^1$H-NMR (300 MHz, CDCl$_3$): δ=7.25 d (J=9 Hz, 2H, aryl); 7.20 d (J=9 Hz, 2H, aryl); 4.78 m (1H, CHOH); 4.44 s (1H, 5-OH); 4.32 dbr (J=6.5 Hz, 1H, H-11); 3.73 m (1H, CH$_2$OH); 3.65 m (1H, CH$_2$OH); 3.54 m (2H, 3-ketal); 3.52 m (J=11.0 Hz, 1H, 3-ketal); 3.44 m (J=11.0 Hz, 1H, 3-ketal); 1.04 s (3H, 3-ketal); 0.87 s (3H, 3-ketal); 0.51 s (3H, H-18).

d) 11β-[4-(1,2-Dihydroxyethyl)phenyl]-20,20,21,21,21-pentafluoro-17-hydroxy-19-nor-17α-pregna-4,9-dien-3-one 200 mg of the compound described under Example 1 c) are stirred in 3 ml of methanol with 141 µl of semiconcentrated aqueous sulfuric acid for one hour at room temperature. The mixture is then poured into saturated aqueous sodium hydrogen carbonate solution and extracted with ethyl acetate. The organic phase is washed with saturated aqueous sodium chloride solution, dried over sodium sulfate, filtered and concentrated under vacuum. Column chromatography on silica gel with a hexane/ethyl acetate mixture gives 78 mg of the title compound as a colorless foam. A mixture of epimers at the benzylcarbinol is obtained.

$^1$H-NMR (300 MHz, CDCl$_3$): δ=7.25 d (J=9 Hz, 2H, aryl); 7.15 d (J=9 Hz, 2H, aryl); 5.77 s (1H, H-4); 4.74 m (1H, CHOH); 4.42 dbr (J=7 Hz, 1H, H-11); 3.69 m (1H, CH$_2$OH); 3.59 m (1H, CH$_2$OH); 0.56 s (3H, H-18).

EXAMPLE 2

Synthesis of 11β-[4-[(1R)-1,2-Dihydroxyethyl]phenyl]-20,20,21,21,21-pentafluoro-17-hydroxy-19-nor-17α-pregna-4,9-dien-3-one a) (R)-1-(4-Bromophenyl)-1,2-ethanediol

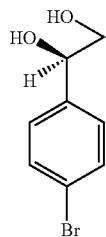

17.0 g of potassium carbonate and 40.4 g of potassium hexacyanoferrate(III) are dissolved in a mixture of 190 ml of n-butanol and 190 ml of water. 30 mg of potassium osmate and 300 mg of (DHQD)2PHAL are then added and the solution is cooled to 0° C. 7.5 g of 4-bromostyrene are then added at 0° C. and the mixture is stirred overnight. It is worked up by the addition of 30 g of sodium sulfite. The reaction solution is extracted with 300 ml of ethyl acetate. The organic phase is dried over sodium sulfate and concentrated to give 7.3 g of a white solid.

Yield: 7.3 g=82.1% of theory $^1$H-NMR (300 MHz, CDCl$_3$): δ=7.50 d (J=9 Hz, 2H, aryl); 7.25 d (J=9 Hz, 2H, aryl); 4.80 dd (J=4.4 Hz+3.6 Hz, 1H); 3.70 m (2H); 2.50 sbr (2H, OH).

The NMR data of the product are consistent with the NMR data described in the literature (T. Barlow, A. Dipple, *Chem. Res. Toxicol.* 1998, 11, 44-53).

b) (R)-4-(4-Bromophenyl)-2,2-dimethyl-1,3-dioxolane

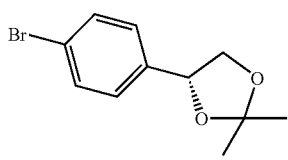

3.5 g of the diol described in Example 2 a) are suspended in 100 ml of acetone. 30 ml of 2,2-dimethoxypropane and 0.3 ml of concentrated sulfuric acid are added. After 2 hours, 100 ml of saturated sodium bicarbonate solution are added to the reaction mixture and the product is extracted with three times 50 ml of ethyl acetate. The organic phases are dried over sodium sulfate and concentrated under vacuum to give 3.7 g of a white solid. FIG. 1 shows the CD spectrum of (R)-4-(4-bromophenyl)-2,2-dimethyl-1,3-dioxolane.

Yield: 3.7 g=58.8% of theory $^1$H-NMR (400 MHz, CDCl$_3$): δ=7.48 d (J=9 Hz, 2H, aryl); 7.25 d (J=9 Hz, 2H, aryl); 5.04 dd (J=9 Hz+8.2 Hz, 1H) 4.30 dd (J=9 Hz+8.2 Hz, 1H); 3.16 dd (J=9 Hz+9 Hz, 1H); 1.53 s (3H); 1.48 s (3H).

c) 20,20,21,21,21-Pentafluoro-17-hydroxy-5,10α-epoxy-19-nor-5α,17α-pregn-9(11)-en-3-one 2,2-dimethylpropane-1,3-diyl ketal

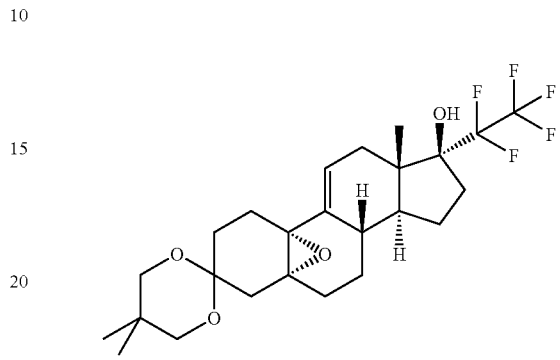

50 g of 5,10-epoxy-5α,10α-estr-9(11)-ene-3,17-dione 3-(2,2-dimethyl-propane-1,3-diyl) ketal (for preparation cf. *Tetrahedron Lett.* 26, 2069-2072 (1985)) are added at −70° C. to 116 g of condensed pentafluoroiodoethane in 500 ml of absolute toluene. 290 ml of a 1.5 molar solution of methyllithium/lithium bromide complex in diethyl ether are added at the same temperature. The reaction mixture is subsequently stirred for one hour at 0° C. It is then added to saturated aqueous ammonium chloride solution and extracted with ethyl acetate. The organic phase is washed with saturated aqueous sodium chloride solution, dried over sodium sulfate and concentrated under vacuum. The crude product is dissolved in 200 ml of acetone, and 450 ml of water are added. The product which precipitates out is filtered off and dried under vacuum.

Yield: 61.6 g (93% of theory)

$^1$H-NMR (500 MHz, CDCl$_3$): δ=6.04 brd (J=2.5 Hz, 1H, vinyl); 3.60 d (J=11.3 1H); 3.46 d (J=11.3 Hz); 3.39 dd (J=11.3 Hz+9.5 Hz, 1H); 2.51 dbr (J=10.6 Hz, 1H); 1.06 s (3H); 0.93 s (3H); 0.85 s (3H).

d) 11β-{4-[(4R)-2,2-Dimethyl-1,3-dioxolan-4-yl]phenyl}20,20,21,21,21-penta-fluoro-5,17-dihydroxy-19-nor-5α,17α-pregn-9-en-3-one 2,2-dimethylpropane-1,3-diyl ketal

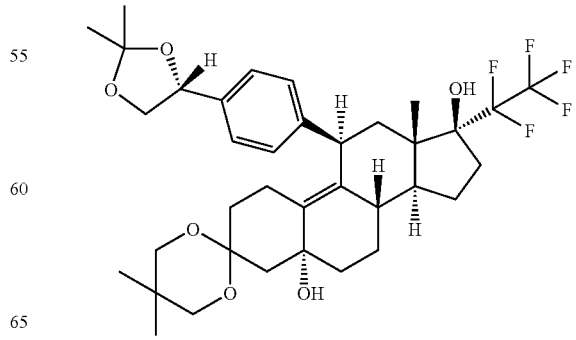

387 mg of magnesium turnings are suspended . . . 3 ml of THF, and 50 µl of dibromoethane are added, with stirring. A solution of 4.35 g of the ketal described in Example 2 b) in 16 ml of THF is slowly added to the suspension at 65° C. The resulting solution is cooled to 0° C. 21.5 mg of CuCl and 2.75 g of the compound prepared in Example 2 c) in 11 ml of THF are added. The reaction mixture is stirred for 2 hours at 20° C. and 28 ml of 10 percent NH₄Cl solution are then added. The reaction mixture is extracted with 20 ml of MTB ether. The organic phase is concentrated and the resulting solid (5.9 g) is purified by chromatography on 120 g of silica gel, with hexane/ethyl acetate as mobile phase, to give 3.2 g of the product as a white solid.

Yield: 3.2 g=85% of theory
¹H-NMR (600 MHz, CDCl₃): δ=7.23 d (J=9 Hz, 2H, aryl); 7.20 d (J=9 Hz, 2H, aryl); 5.03 dd (J=9 Hz+8.4 Hz, 1H); 4.46 s (1H, OH); 4.33 dbr (J=6.5 Hz, 1H); 4.27 dd (J=9 Hz+8.4 Hz, 1H); 3.68 dd (J=9 Hz+9 Hz, 1H); 1.56 s (3H); 1.49 s (3H); 1.07 s (3H); 0.86 s (3H); 0.50 s (3H).

e) 11β-[4-[(1R)-1,2-Dihydroxyethyl]phenyl]-20,20,21,21,21-pentafluoro-17-hydroxy-19-nor-17α-pregna4,9-dien-3-one

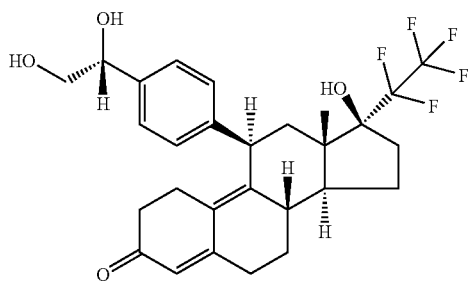

Figure 2:
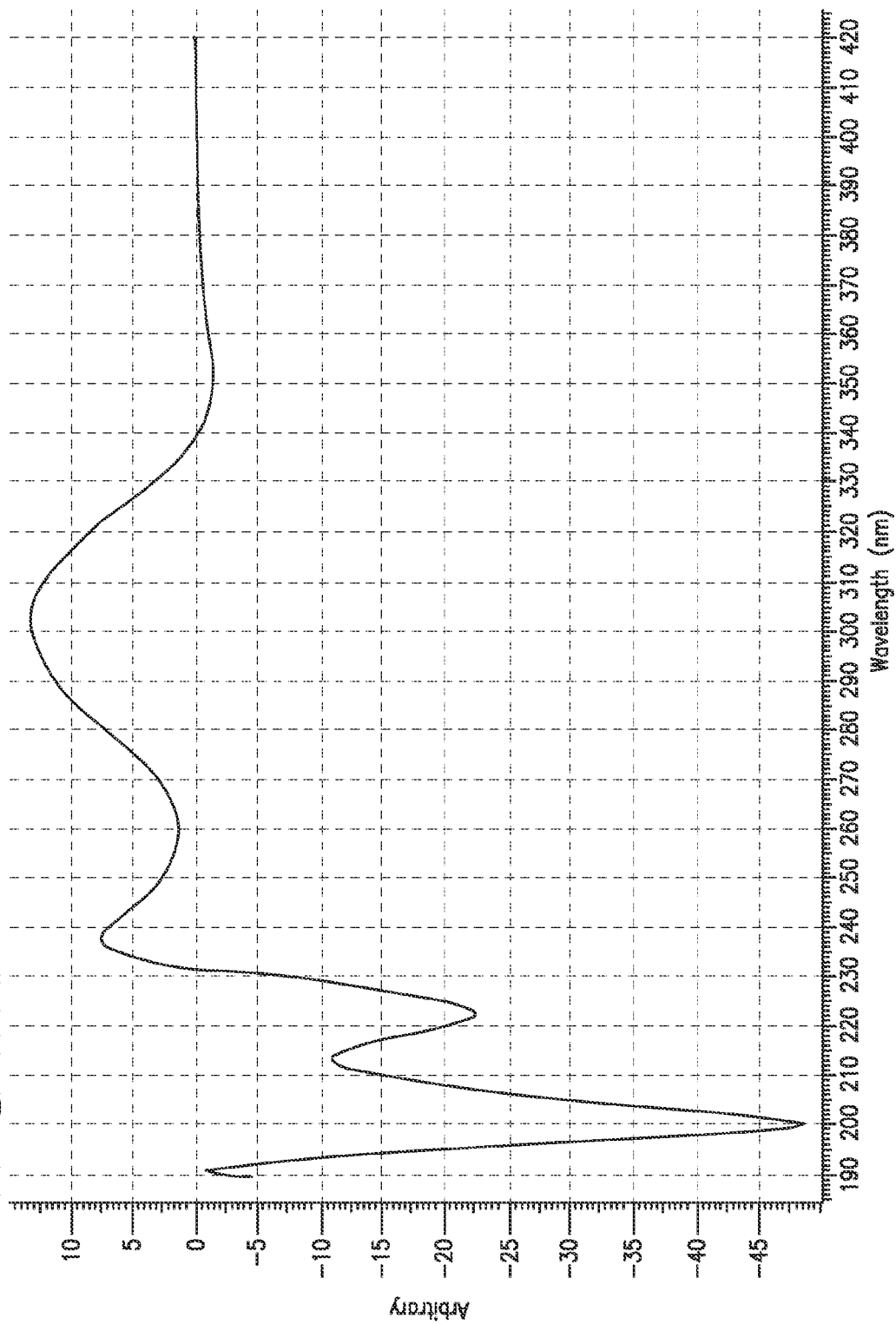

2.5 g of the compound described under Example 2 d) are dissolved in 20 ml of THF, 2.5 ml of semiconcentrated aqueous sulfuric acid are added and the reaction mixture is stirred for three hours at 20° C. It is then poured into 60 ml of saturated aqueous sodium hydrogen carbonate solution and extracted with ethyl acetate. Purification by column chromatography on silica gel with a dichloromethane/acetone mixture gives 1.2 g of the title compound as a colorless foam. FIG. 2 shows the CD spectrum of 11β-[4-[(1R)-1,2-Dihydroxyethyl]phenyl]-20,20,21,21,21-pentafluoro-17-hydroxy-19-nor-17α-pregna-4,9-dien-3-one.

Yield: 1.2 g=61.2% of theory
¹H-NMR (300 MHz, CDCl₃): δ=7.25 d (J=9 Hz, 2H, aryl); 7.15 d (J=9 Hz, 2H, aryl); 5.77 s (1H, H-4); 4.74 m (1H, CHOH); 4.42 dbr (J=7 Hz, 1H, H-11); 3.69 m (1H, CH₂OH); 3.59 m (1H, CH₂OH); 0.56 s (3H, H-18).

EXAMPLE 3a

Synthesis of 20,20,21,21,21-pentafluoro-17-hydroxy-11β-[4-(hydroxyacetyl)phenyl]-19-nor-17α-pregna-4,9-dien-3-one a) 20,20,21,21,21-Pentafluoro-11β-[4-(hydroxyacetyl)phenyl]-5,17-dihydroxy-19-nor-5α, 17α-pregn-9-en-3-one 2,2-dimethylpropane-1,3-diyl ketal 283 µl of tert-butyl hydroperoxide are added dropwise at room temperature to 3.6 mg of chromium trioxide in 7 ml of dichloromethane. A solution of 450 mg of the compound prepared under Example 1 c) in 7 ml of dichloromethane is then added dropwise. The mixture is stirred for three hours at room temperature. The reaction is stopped by the addition of dimethyl sulfide. The mixture is washed with saturated aqueous sodium chloride solution, dried over sodium sulfate and concentrated under vacuum. Chromatography of the resulting crude product on silica gel with a hexane/ethyl acetate mixture gives 87 mg of the title compound as a white foam.

¹H-NMR (300 MHz, CDCl₃): δ=7.83 d (J=9 Hz, 2H, aryl); 7.37 d (J=9 Hz, 2H, aryl); 4.84 m (2H, CH₂OH); 4.37 dbr (J=6.5 Hz, 1H, H-11); 3.53 m (2H, 3-ketal); 3.47 m (J=11.0 Hz, 1H, 3-ketal); 3.42 m (J=11.0 Hz, 1H, 3-ketal); 1.04 s (3H, 3-ketal); 0.85 s (3H, 3-ketal); 0.49 s (3H, H-18).

b) 20,20,21,21,21-Pentafluoro-17-hydroxy-11β-[4-(hydroxyacetyl)phenyl]-19-nor-17α-pregna-4,9-dien-3-one Analogously to the process described in Example 1 d), 87 mg of the compound described under 3 a) are reacted in 1.4 ml of methanol with 62 µl of semiconcentrated aqueous sulfuric acid to give 25 mg of the title compound as a colorless foam.

¹H-NMR (300 MHz, CDCl₃): δ=7.86 d (J=9 Hz, 2H, aryl); 7.34 d (J=9 Hz, 2H, aryl); 5.81 s (1H, H-4); 4.85 dbr (J=5 Hz, 2H, CH₂OH); 4.50 dbr (J=7 Hz, 1H, H-11); 3.50 tbr (J=5 Hz, 1H, OH); 0.57 s (3H, H-18).

EXAMPLE 3b

Alternative Synthesis of 20,20,21,21,21-pentafluoro-17-hydroxy-11β-[4-(hydroxyacetyl)phenyl]-19-nor-17α-pregna-4,9-dien-3-one a) [[2-(4-Bromophenyl)-1,3-dioxolan-2-yl]methoxy](1,1-dimethylethyl)dimethylsilane

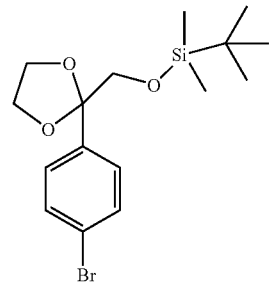

73.5 g 2-(4-Bromophenyl)-1,3-dioxolane-2-methanol are dissolved in 800 ml N,N-dimethylformamide. 38.6 g imidazole and 51.3 g tert-butyldimethylchlorosilane were added. It was stirred for 12 hours at 23° C. Afterwards, the reaction mixture was poured into a saturated aqueous solution of sodium bicarbonate. It was stirred for another 30 min. Then it was extracted with ethyl acetate twice. The combined organic layers were washed with brine and dried over sodium sulphate. The crude product was purified by column chromatography. 103.21 g product was obtained (97.5% of theory).

$^1$H-NMR (300 MHz, CDCl$_3$): δ=7.45 d (J=9 Hz, 2H, aryl); 7.37 d (J=9 Hz, 2H, aryl); 4.08 m (2H, ketal); 3.84 m (2H, ketal), 0.83 s (9H, t-butyl-Si); -0.05 s (6H, Me-Si).

b) 11β-[4-[2-[[[(1,1-Dimethylethyl)dimethylsilyl]oxy]methyl]-1,3-dioxolan-2-yl]phenyl]-20,20,21,21,21-pentafluoro-5,17-dihydroxy-19-nor-5α,17α-pregn-9-en-3-one 2,2-dimethylpropane-1,3-diyl ketal

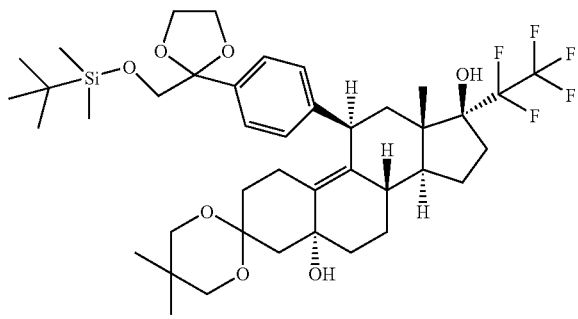

0.3 ml dibromoethane was added to a suspension of 6.22 g magnesium turnings in 80 ml THF. Afterwards, a solution of 95.5 g 3ba) in 900 ml THF was added slowly. The temperature was kept below 50° C. Afterwards, it was stirred at 50° C. for 1 h. Then, the reaction mixture was cooled to 0° C. and 400 mg CuCl was added. After the stirring was continued for another 10 minutes, a solution of 20 g of the compound described under 2c) in 200 ml THF was added at 0° C. The mixture was stirred for 2 hours at 0° C. and then allowed to warm up to 23° C. Stirring was continued for another 12 hours at 23° C. Then the reaction mixture was poured into a saturated solution of ammonium chloride. It was stirred for another 30 minutes and afterwards it was extracted with ethyl acetate 3 times. The combined organic layers were washed with brine and dried over sodium sulphate. The crude product was purified by column chromatography. 31 g product was obtained (97% of theory).

$^1$H-NMR (300 MHz, CDCl$_3$): δ=7.40 d (J=9 Hz, 2H, aryl); 7.20 d (J=9 Hz, 2H, aryl); 4.49 s (1H, OH); 4.36 dbr (J=6.5 Hz, 1H); 4.12 m (2H, ketal), 3.90 (2H, ketal), 3.79 m (4H, ketal); 3.50 m (2H), 1.09 s (3H); 0.94 s (3H); 0.90 (9H, t-butyl-Si), 0.57 s (3H); 0.00 (6H, Me-Si).

c) 20,20,21,21,21-Pentafluoro-5,17-dihydroxy-11β-[4-[2-(hydroxymethyl)-1,3-dioxolan-2-yl]phenyl]-19-nor-5α, 17α-pregn-9-en-3-one 2,2-dimethylpropane-1,3-diyl ketal

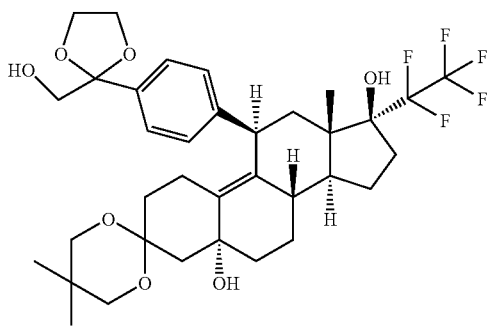

Tetrabutylammonium fluoride (0.6 ml of a 1 molar solution in THF) was added to a solution of 470 mg compound 3bb) in 5 ml THF. It was stirred for 2 hours at 23° C. Then, the reaction mixture was poured into a saturated solution of ammonium chloride. It was stirred for another 30 minutes and afterwards it was extracted with ethyl acetate. The organic layer was washed with brine and dried over sodium sulphate. The crude product was purified by column chromatography. 318 mg product was obtained (80% of theory).

$^1$H-NMR (300 MHz, CDCl$_3$): δ=7.34 d (J=9 Hz, 2H, aryl); 7.18 d (J=9 Hz, 2H, aryl); 4.44 s (1H, OH); 4.30 dbr (J=6.5 Hz, 1H, H-11); 4.10 m (2H, ketal), 3.88 m (2H, ketal); 3.70 m (4H, ketal), 3.50 m (2H); 1.02 s (3H); 0.88 s (3H); 0.50 s (3H).

dα) 20,20,21,21,21-Pentafluoro-17-hydroxy-11β-[4-(hydroxyacetyl)phenyl]-19-nor-17α-pregna-4,9-dien-3-one from 3bb

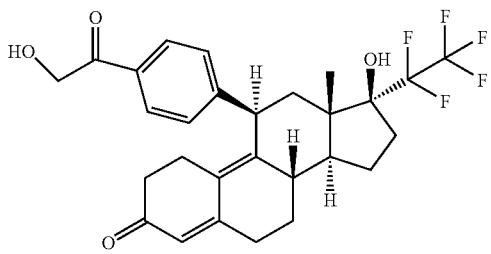

15 ml of semiconcentrated aqueous sulfuric acid were added to a solution of 15 g of the compound described under example 3bb in 150 ml THF. It was stirred for 2.5 hours at 23° C. Afterwards, the reaction mixture was poured into saturated aqueous sodium hydrogen carbonate solution. It was stirred for another 30 minutes and afterwards extracted with ethyl acetate. The organic layer was washed with brine and dried over sodium sulphate. The crude product was purified by column chromatography. 7.99 g product was obtained (80% of theory).

dβ) 20,21,21,21-Pentafluoro-17-hydroxy-11β-[4-(hydroxyacetyl)phenyl]-17α-pregna-4,9-dien-3-one from 3bc Reaction of 300 mg 3bc with semiconcentrated aqueous sulfuric acid in THF in analogy to the procedure described under example 3dα yielded 198 mg (85% of theory) product.

EXAMPLE 4

Abortion Test on Female Rats

The antigestagenic action of the progesterone receptor antagonists according to the invention was tested on pregnant rats (6 rats per group) on days 5 to 7 post coitum under conventional housing and feeding conditions.

After successful copulation, the pregnant animals (presence of sperm in the vaginal smear on day 1 of pregnancy=d1 p.c.) were randomized and divided up into the treatment group and the control group. Each animal was then injected subcutaneously with 1.5 mg/kg of the test substance (11β-[4-(1,2-Dihydroxyethyl)phenyl]-20,20,21,21,21-pentafluoro-17-hydroxy-19-nor-17α-pregna-4,9-dien-3-one according to Example 1 or 20,20,21,21,21-pentafluoro-17-hydroxy-11β-[4-(hydroxyacetyl)phenyl]-19-nor-17α-pregna-4,9-dien-3-one according to Example 3) or 1.0 ml/kg of vehicle (benzyl benzoate/castor oil: 1+4[v/v]) daily from day 5 to day 7 (d5-d7 p.c.).

The autopsy was performed on day 9 (d9 p.c.). As the parameter of antigestagenic action, the uterus was examined for the presence of implantation sites. The complete absence of implantation sites as well as the presence of pathological, hemorrhagic or otherwise abnormal implantation sites on day 9 (d9 p.c.) were evaluated as abortions. The results of the abortion test are shown in Table 1.

TABLE 1

Results of the abortion test

| Test substance | Daily dose [mg/kg] | Abortion rate [%] |
|---|---|---|
| 11β-[4-(1,2-Dihydroxyethyl)phenyl]-20,20,21,21,21-pentafluoro-17-hydroxy-19-nor-17α-pregna-4,9-dien-3-one (Example 1) | 1.5 | 100 |
| 20,20,21,21,21-Pentafluoro-17-hydroxy-11β-[4-(hydroxyacetyl)phenyl]-19-nor-17α-pregna-4,9-dien-3-one (Example 3) | 1.5 | 100 |

EXAMPLE 5

Determination of the McPhail Index on the Rabbit

The antigestagenic efficacy of the progesterone receptor antagonists according to the invention was tested on 35-day-old rabbits under conventional housing and feeding conditions.

As a preparatory measure, the animals were treated subcutaneously with 5.0 μg/kg/d with 17β-estradiol from day 1 to day 4. To determine the antigestagenic efficacy, the animals were treated subcutaneously from day 7 to day 10 with 0.2 mg/kg/d of progesterone and 3 mg/kg/d of the test substance (11β-[4-(1,2-Dihydroxyethyl)phenyl]-20,20,21,21,21-pentafluoro-17-hydroxy-19-nor-17α-pregna-4,9-dien-3-one according to Example 1 or 20,20,21,21,21-pentafluoro-17-hydroxy-11β-[4-(hydroxyacetyl)phenyl]-19-nor-17α-pregna-4,9-dien-3-one according to Example 3) simultaneously. The vehicle used was a mixture of benzyl benzoate and castor oil in a ratio of 1+4 (v/v).

The autopsy was performed on day 11 after the start of treatment. The uteri were removed and fixed for histology. The McPhail index (degree of glandular differentiation) was determined by means of light microscopy (evaluation: 1=no glandular differentiation; 4=maximum glandular differentiation) as the parameter of antigestagenic efficacy (inhibition of the glandular differentiation caused by progesterone). The resulting McPhail index is shown in Table 2.

TABLE 2

McPhail index

| Test substance | Daily dose [mg/kg] | McPhail index [median] |
|---|---|---|
| 11β-[4-(1,2-Dihydroxyethyl)phenyl]-20,20,21,21,21-pentafluoro-17-hydroxy-19-nor-17α-pregna-4,9-dien-3-one (Example 1 + progesterone) | 3.0 + 0.2 | 1.0 |
| 20,20,21,21,21-Pentafluoro-17-hydroxy-11β-[4-(hydroxyacetyl)phenyl]-19-nor-17α-pregna-4,9-dien-3-one (Example 3 + progesterone) | 3.0 + 0.2 | 1.0 |

EXAMPLE 6a

Metabolic stability of 11β-[4-(1,2-Dihydroxyethyl)phenyl]-20,20,21,21,21-pentafluoro-17-hydroxy-19-nor-17α-pregna-4,9-dien-3-one and 20,20,21,21,21-pentafluoro-17-hydroxy-11β-[4-(hydroxyacetyl)-phenyl]-19-nor-17α-pregna-4,9-dien-3-one in human liver microsomes (HLM)

Human liver microsomes (HLM) were used to assess the metabolic stability of substances of general formula I.

The incubations were carried out in duplicate with HLM and an NADPH-generating system using a shaker bath at 37° C. The incubation mixture (consisting of cofactor solution, potassium phosphate buffer and microsome preparation) was freshly prepared according to the Table below.

| Buffer | Potassium phosphate, 100 mM, pH 7.4 |
|---|---|
| Reconstitution system in buffer: | |
| NADP | 1.2 mM |
| Glucose-6-phosphate | 8.0 mM |
| Glucose-6-phosphate dehydrogenase | 1.4 units/ml |
| $MgCl_2$ | 5.0 mM |
| KCl | 38.0 mM |
| Protein concentration (HLM) | 1.0 mg/ml |

The incubation volume was 0.25 ml. The incubation mixture was preincubated for three minutes at 37° C. The reaction was started by the addition of the test substance (final concentration 50 μM). The reaction was ended after an incubation time of 60 minutes by the addition of 250 μl of methanol and the mixture was then centrifuged to pellet the protein. The samples were stored at −18° C. for subsequent RP-HPLC analysis.

According to RP-HPLC analysis, about 70% of the 11β-[4-1,2-Dihydroxyethyl)phenyl]-20,20,21,21,21-pentafluoro-17-hydroxy-19-nor-17α-pregna-4,9-dien-3-one used and about 80% of the 20,20,21,21,21-penta-fluoro-17-hydroxy-11β-[4-(hydroxyacetyl)phenyl]-19-nor-17α-pregna-4,9-dien-3-one used were recovered in the supernatant.

EXAMPLE 6b

Metabolic stability of 11β-(4-acetylphenyl)-20,20,21,21,21-pentafluoro-17-hydroxy-19-nor-17α-pregna-4,9-dien-3-one in human liver microsomes (HLM)

Human liver microsomes (HLM) were used to assess the metabolic stability of substances of general formula I.

The incubations were carried out in duplicate with HLM and an NADPH-generating system using a shaker bath at 37° C. The incubation mixture (consisting of cofactor solution, potassium phosphate buffer and microsome preparation) was freshly prepared according to the Table below.

| Buffer | Potassium phosphate, 100 mM, pH 7.4 |
|---|---|
| Reconstitution system in buffer: | |
| NADP | 1.2 mM |
| Glucose-6-phosphate | 8.0 mM |
| Glucose-6-phosphate dehydrogenase | 1.4 units/ml |
| MgCl$_2$ | 5.0 mM |
| KCl | 38.0 mM |
| Protein concentration (HLM) | 0.4 mg/ml |

The incubation volume was 0.25 ml. The incubation mixture was preincubated for three minutes at 37° C. The reaction was started by the addition of the test substance (final concentration 10 μM). The reaction was ended after an incubation time of 60 minutes by the addition of 250 μl of methanol and the mixture was then centrifuged to pellet the protein. The samples were stored at −18° C. for subsequent RP-HPLC analysis.

According to RP-HPLC analysis, 60% of the 11β-(4-acetylphenyl)-20,20,21,21,21-pentafluoro-17-hydroxy-19-nor-17α-pregna-4,9-dien-3-one used was recovered in the supernatant.

EXAMPLE 7

Antigestagenic action of 11β-[4-(1,2-dihydroxyethyl)phenyl]-20,20,21,21,21-pentafluoro-17-hydroxy-19-nor-17α-pregna-4,9-dien-3-one and 20,20,21,21,21-pentafluoro-17-hydroxy-11β-[4-(hydroxyacetyl)-phenyl]-19-nor-17α-pregna-4,9-dien-3-one in stable transfectands of human neuroblastoma cells (SK-N-MC cells) with human progesterone A or progesterone B receptor and an MTV-LUC reporter construct SK-N-MC cells (human neuroblastoma cells), stably transfected with plasmids, which express human progesterone receptor B (pRChPR-B-neo) or human progesterone receptor A (pRChPR-A-neo) and a reporter construct (pMMTV-LUC), were incubated for 24 hours, either in the absence (negative control) or in the presence of increasing amounts of 11β-[4-(1,2-dihydroxy-ethyl)phenyl]-20,20,21,21,21-pentafluoro-17-hydroxy-19-nor-17α-pregna-4,9-dien-3-one or 20,20,21,21,21-pentafluoro-17-hydroxy-11β-[4-(hydroxyacetyl)-phenyl]-19-nor-17α-pregna-4,9-dien-3-one (0.01 nmol/l, 0.1 nmol/l, 1 nmol/l, 10 nmol/l, 100 nmol/l and 1 μmol/l), in order to determine the agonistic efficacy. As a positive control of reporter gene induction, the cells were treated with the synthetic gestagen promegestone (0.01 nmol/l, 0.1 nmol/l, 1 nmol/l, 10 nmol/l, 100 nmol/l and 1 μmol/l). To determine the antagonistic activity, the cells were treated with 0.1 nmol/l of promegestone and additionally with increasing amounts of 11β-[4-(1,2-dihydroxyethyl)phenyl]-20,20,21,21-pentafluoro-17-hydroxy-19-nor-17α-pregna-4,9-dien-3-one or 20,20,21,21,21-pentafluoro-17-hydroxy-11β-[4-(hydroxyacetyl)phenyl]-19-nor-17α-pregna-4,9-dien-3-one (0.01 nmol/l, 0.1 nmol/l, 1 nmol/l, 10 nmol/l, 100 nmol/l and 1 μmol/l). As a positive control of the inhibition of reporter gene transcription, the cells were incubated with increasing amounts of the progesterone receptor antagonist 11β-(4-acetylphenyl)-20,20,21,21,21-pentafluoro-17-hydroxy-19-nor-17α-pregna-4,9-dien-3-one (1 pmol/l, 0.01 nmol/l, 0.1 nmol/l, 1 nmol/l, 10 nmol/l and 100 nmol/l). The activity of the LUC reporter gene (LUC=luciferase) was determined in the cell lyzates and measured as RLU (relative light units). All the measured values are given as % efficacy (relative LUC activity as mean plus/minus standard deviation (n=3 experiments)) and as $EC_{50}$ or $IC_{50}$ concentrations.

a) Agonistic Activity:

Neither 11β-[4-(1,2-dihydroxyethyl)phenyl]-20,20,21,21,21-pentafluoro-17-hydroxy-19-nor-17α-pregna-4,9-dien-3-one nor 20,20,21,21,21-pentafluoro-17-hydroxy-11β-[4-(hydroxyacetyl)phenyl]-19-nor-17α-pregna-4,9-dien-3-one exhibits induction of the LUC activity on PR-A or PR-B (in contrast to the promegestone positive control, which induces the reporter gene as a function of dose). Table 3 shows the agonistic activity of the two test substances and promegestone.

TABLE 3

Agonistic activity of 11β-[4-(1,2-dihydroxyethyl)phenyl]-20,20,21,21,21-pentafluoro-17-hydroxy-19-nor-17α-pregna-4,9-dien-3-one or 20,20,21,21,21-pentafluoro-17-hydroxy-11β-[4-(hydroxyacetyl)phenyl]-19-nor-17α-pregna-4,9-dien-3-one

| | Progesterone receptor A (PR-A) | | Progesterone receptor B (PR-B) | |
|---|---|---|---|---|
| Compound | Potency $EC_{50}$ [nmol/l] | Efficacy [%] | Potency $EC_{50}$ [nmol/l] | Efficacy [%] |
| Promegestone | 0.23 ± 0.03 (n = 3) | 100 (n = 3) | 0.03 ± 0.00 (n = 3) | 100 (n = 3) |

TABLE 3-continued

Agonistic activity of 11β-[4-(1,2-dihydroxyethyl)phenyl]-20,20,21,21,21-pentafluoro-17-hydroxy-19-nor-17α-pregna-4,9-dien-3-one or 20,20,21,21,21-pentafluoro-17-hydroxy-11β-[4-(hydroxyacetyl)phenyl]-19-nor-17α-pregna-4,9-dien-3-one

| Compound | Progesterone receptor A (PR-A) | | Progesterone receptor B (PR-B) | |
|---|---|---|---|---|
| | Potency $EC_{50}$ [nmol/l] | Efficacy [%] | Potency $EC_{50}$ [nmol/l] | Efficacy [%] |
| 11β-[4-(1,2-Dihydroxyethyl)phenyl]-20,20,21,21,21-pentafluoro-17-hydroxy-19-nor-17α-pregna-4,9-dien-3-one | 0 ± 0 (n = 3) | no effect (n = 3) | 0 ± 0 (n = 3) | no effect (n = 3) |
| 20,20,21,21,21-Pentafluoro-17-hydroxy-11β-[4-(hydroxyacetyl)phenyl]-19-nor-17α-pregna-4,9-dien-3-one | 0 ± 0 (n = 3) | no effect (n = 3) | 0 ± 0 (n = 3) | no effect (n = 3) | b) Antagonistic Activity:

11β-[4-(1,2-Dihydroxyethyl)phenyl]-20,20,21,21,21-pentafluoro-17-hydroxy-19-nor-17α-pregna4,9-dien-3-one and 20,20,21,21,21-pentafluoro-17-hydroxy-11β-[4-(hydroxyacetyl)phenyl]-19-nor-17α-pregna-4,9-dien-3-one exhibited dose-dependent inhibition of the LUC activity induced by 0.1 nmol/l of promegestone (100%) at both progesterone receptor isoforms. Table 4 shows the agonistic activity of the two test substances compared with 11β-(4-acetylphenyl)-20,20,21,21,21-pentafluoro-17-hydroxy-19-nor-17α-pregna-4,9-dien-3-one. The stably transfected cell lines express approximately 500 fm (femtomol) of PR-A or PR-B.

TABLE 4

Antagonistic activity of 11β-[4-(1,2-dihydroxyethyl)phenyl]-20,20,21,21,21-pentafluoro-17-hydroxy-19-nor-17α-pregna-4,9-dien-3-one or 20,20,21,21,21-pentafluoro-17-hydroxy-11β-[4-(hydroxyacetyl)phenyl]-19-nor-17α-pregna-4,9-dien-3-one

| Compound | Progesterone receptor A (PR-A) | | Progesterone receptor B (PR-B) | |
|---|---|---|---|---|
| | Potency $IC_{50}$ [nmol/l] | Efficacy [%] | Potency $IC_{50}$ [nmol/l] | Efficacy [%] |
| 11β-(4-Acetylphenyl)-20,20,21,21,21-pentafluoro-17-hydroxy-19-nor-17α-pregna-4,9-dien-3-one | 0.014 ± 0.01 (n = 2) | 100 ± 0 (n = 2) | 0.02 ± 0.01 (n = 3) | 100 ± 0 (n = 3) |
| 11β-[4-(1,2-Dihydroxyethyl)phenyl]-20,20,21,21,21-pentafluoro-17-hydroxy-19-nor-17α-pregna-4,9-dien-3-one | 1.87 ± 0.23 (n = 3) | 100 ± 0 (n = 3) | 3.47 ± 0.46 (n = 3) | 100 ± 0 (n = 3) |
| 20,20,21,21,21-Pentafluoro-17-hydroxy-11β-[4-(hydroxyacetyl)phenyl]-19-nor-17α-pregna-4,9-dien-3-one | 0.18 ± 0.06 (n = 3) | 100 ± 0 (n = 3) | 0.28 ± 0.08 (n = 3) | 100 ± 0 (n = 3) |

These data show that 11β-[4-(1,2-dihydroxyethyl)phenyl]-20,20,21,21,21-pentafluoro-17-hydroxy-19-nor-17α-pregna-4,9-dien-3-one and 20,20,21,21,21-pentafluoro-17-hydroxy-11β-[4-(hydroxyacetyl)phenyl]-19-nor-17α-pregna-4,9-dien-3-one are pure antagonists of both progesterone receptor isoforms in SK-N-MC cells which stably express progesterone receptor A or progesterone receptor B. Neither compound exhibits any selectivity in respect of one progesterone receptor isoform. However, 11β-[4-(1,2-dihydroxyethyl)phenyl]-20,20,21,21,21-pentafluoro-17-hydroxy-19-nor-17α-pregna-4,9-dien-3-one is about 130 times less potent than 11β-(4-acetyl-phenyl)-20,20,21,21,21-pentafluoro-17-hydroxy-19-nor-17α-pregna-4,9-dien-3-one at the progesterone receptors. 20,20,21,21,21-Pentafluoro-17-hydroxy-11β-[4-(hydroxyacetyl)phenyl]-19-nor-17α-pregna-4,9-dien-3-one is about 13 times weaker than 11β-(4-

In the foregoing and in the examples, all temperatures are set forth uncorrected in degrees Celsius and, all parts and percentages are by weight, unless otherwise indicated.

The entire disclosures of all applications, patents and publications, cited herein and of corresponding European application No. 10 2006 054 535.5, filed Nov. 15, 2006, and U.S. Provisional Application Ser. No. 60/858,955, filed Nov. 15, 2006, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A progesterone receptor antagonist of formula I:

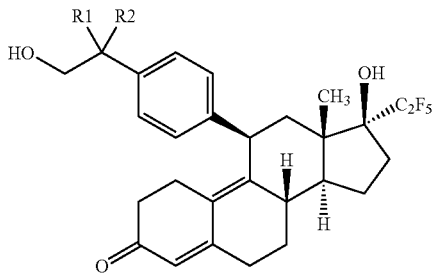

formula I in which R1 is a hydrogen atom and R2 a hydroxyl group or R1 and R2 together are an oxo group.

2. 11β-[4-(1,2-Dihydroxyethyl)phenyl]-20,20,21,21,21-pentafluoro-17-hydroxy-19-nor-17α-pregna-4,9-dien-3-one.

3. 11 β-[4-[(1R)-1,2-Dihydroxyethyl]phenyl]-20,20,21,21,21-pentafluoro-17-hydroxy-19-nor-17α-pregna-4,9-dien-3-one.

4. 11β-[4-[(1S)-1,2-Dihydroxyethyl]phenyl]-20,20,21,21,21-pentafluoro-17-hydroxy-19-nor-17α-pregna-4,9-dien-3-one.

5. 20,20,21,21,21-Pentafluoro-17-hydroxy-11β-[4-(hydroxyacetyl)phenyl]-19-nor-17α-pregna-4,9-dien-3-one.

6. The compound of claim 1, in isolated form.

7. The compound of claim 3, free of 11β-[4-[(1S)-1,2-Dihydroxyethyl]phenyl]-20,20,21,21,21-pentafluoro-17-hydroxy-19-nor-17α-pregna-4,9-dien-3-one.

8. The compound of claim 4, free of 11β-[4-[(1R)-1,2-Dihydroxyethyl]phenyl]-20,20,21,21,21-pentafluoro-17-hydroxy-19-nor-17α-pregna-4,9-dien-3-one.

9. A pharmaceutical composition comprising a progesterone receptor antagonist as claimed in claim 1, and a pharmaceutically acceptable carrier.

10. The composition as claimed in claim 9 comprising 11β-[4-(1,2-dihydroxyethyl)phenyl]-20,20,21,21,21-pentafluoro-17-hydroxy-19-nor-17α-pregna-4,9-dien-3-one.

11. The composition as claimed in claim 10 comprising 11β-[4-[(1R)-1,2-dihydroxyethyl]phenyl]-20,20,21,21,21-pentafluoro-17-hydroxy-19-nor-17α-pregna-4,9-dien-3-one.

12. The composition as claimed in claim 10 comprising 11β-[4-[(1S)-1,2-dihydroxyethyl]phenyl]-20,20,21,21,21-pentafluoro-17-hydroxy-19-nor-17α-pregna-4,9-dien-3-one.

13. The composition as claimed in claim 6 comprising 20,20,21,21,21-pentafluoro-17-hydroxy-11β-[4-(hydroxyacetyl)phenyl]-19-nor-17α-pregna-4,9-dien-3-one.

14. A pharmaceutical composition of claim 9, adapted for oral administration.

15. A pharmaceutical composition of claim 9, which contains from 0.01 mg to 100 mg of the antagonist.

16. A method for the treatment of endometriosis, myoma or hormone-dependent tumors, comprising administering to a host in need thereof an effective amount of a progesterone receptor antagonist of claim 1.

17. A method according to claim 16, wherein the antagonist is 11β-[4-(1,2-dihydroxyethyl)phenyl]-17β-hydroxy-17α-(1,1,2,2,2-pentafluoroethyl)estra-4,9-dien-3-one.

18. A method according to claim 17, wherein the antagonist is containing 11β-[4-[(1R)-1,2-dihydroxyethyl]phenyl]-20,20,21,21,21-pentafluoro-17-hydroxy-19-nor-17α-pregna-4,9-dien-3-one.

19. A method according to claim 17, wherein the antagonist is 11 β-[4-[(1S)-1,2-dihydroxyethyl]phenyl]-20,20,21,21,21-pentafluoro-17-hydroxy-19-nor-17α-pregna-4,9-dien-3-one.

20. A method according to claim 16, wherein the antagonist is 20,20,21,21,21-pentafluoro-17-hydroxy-11β-[4-(hydroxyacetyl)phenyl]-19-nor-17α-pregna-4,9-dien-3-one.

21. A method for the treatment of endometriosis or carcinoma of the breast, comprising administering to a host in need thereof an effective amount of an antagonist of claim 1.

22. A method for the treatment of myoma, comprising administering to a host in need thereof an effective amount of an antagonist of claim 1.

23. A process for the preparation of an antagonist of claim 1, comprising employing as an intermediate 11β-(4-Ethenylphenyl)-20,20,21,21,21-pentafluoro-5,17-dihydroxy-19-nor-5α,17α-pregn-9-en-3-one 2,2-dimethylpropane-1,3-diyl ketal.

24. A process for the preparation of an antagonist of claim 1, comprising employing as an intermediate 11β-[4-(1,2-Dihydroxyethyl)phenyl]-20,20,21,21,21-pentafluoro-5,17-dihydroxy-19-nor-5α,17α-pregn-9-en-3-one 2,2-dimethylpropane-1,3-diyl ketal.

25. A process for the preparation of an antagonist of claim 1, comprising employing as an intermediate 20,20,21,21,21-Pentafluoro-17-hydroxy-5,10α-epoxy-19-nor-5α,17α-pregn-9(11)-en-3-one 2,2-dimethylpropane-1,3-diyl ketal.

26. A process for the preparation of an antagonist of claim 1, comprising employing as an intermediate 11β-{4-[(4R)-2,2-Dimethyl-1,3-dioxolan-4-yl]phenyl}-20,20,21,21,21-pentafluoro-5,17-dihydroxy-19-nor-5α,17α-pregn-9-en-3-one 2,2-dimethylpropane-1,3-diyl ketal.

27. A process for the preparation of progesterone receptor antagonist 20,20,21,21,21-Pentafluoro-17-hydroxy-11i-[4-(hydroxyacetyl)phenyl]-19-nor-17α-pregna-4,9-dien-3-one comprising employing as an intermediate 11β-[4-[2-[[[(1,1-Dimethylethyl)dimethylsilyl]oxy]methyl]-1,3-dioxolan-2-yl]phenyl]-20,20,21,21,21-pentafluoro-5,17-dihydroxy-19-nor-5α,17α-pregn-9-en-3-one 2,2-dimethylpropane-1,3-diyl ketal.

28. A process for the preparation of progesterone receptor antagonist 20,20,21,21,21-Pentafluoro-17-hydroxy-11i-[4-(hydroxyacetyl)phenyl]-19-nor-17α-pregna-4,9-dien-3-one comprising employing as an intermediate 20,20,21,21,21-Pentafluoro-5,17-dihydroxy-11β-[4-[2-(hydroxymethyl)-1,3-dioxolan-2-yl]phenyl]-19-nor-5α,17α-pregn-9-en-3-one 2,2-dimethylpropane-1,3-diyl ketal.

* * * * *

UNITED STATES PATENT AND TRADEMARK OFFICE
CERTIFICATE OF CORRECTION

PATENT NO. : 8,053,426 B2
APPLICATION NO. : 11/984331
DATED : November 8, 2011
INVENTOR(S) : Fuhrmann et al.

It is certified that error appears in the above-identified patent and that said Letters Patent is hereby corrected as shown below:

Column 18, line 7 reads "nist is containing 11β-[4-[(1R)-1,2-dihydroxyethyl]phenyl]-"
should read -- nist is 11β-[4-[(1R)-1,2-dihydroxyethyl]phenyl]- --

Signed and Sealed this
Twenty-first Day of February, 2012

David J. Kappos
*Director of the United States Patent and Trademark Office*